United States Patent [19]

Guillot

[11] 4,317,457

[45] Mar. 2, 1982

[54] ELECTROCONDUCTING CAST FORMING A CUTANEOUS ELECTRODE FOR APPLYING ELECTRICAL CURRENTS TO THE HUMAN BODY FOR THERAPEUTIC OR AESTHETIC TREATMENT AND METHOD OF USING SUCH ELECTROCONDUCTING CAST

[76] Inventor: Jacqueline Guillot, 13, Allée de l'Entente, 93130 Noisy-le-Sec, France

[21] Appl. No.: 24,370

[22] Filed: Mar. 27, 1979

[30] Foreign Application Priority Data

Mar. 28, 1978 [FR] France ............................. 78 08845

[51] Int. Cl.³ .............................................. A61N 1/18
[52] U.S. Cl. ..................................... 128/783; 128/792; 128/802; 128/207.21
[58] Field of Search ..................... 128/362, 379–382, 128/390, 783, 792, 795, 796, 798, 802, 803, 82.1, 419 F, 207.21, 639–641; 252/518

[56] References Cited

U.S. PATENT DOCUMENTS

| 1,973,911 | 9/1934 | Ruben ................................. 128/798 |
| 3,528,408 | 9/1970 | Opperman ........................... 128/640 |
| 3,565,059 | 2/1971 | Hauser et al. ...................... 128/640 |
| 3,607,788 | 9/1971 | Adolph et al. .................. 128/640 X |
| 3,989,050 | 11/1976 | Buchalter ....................... 128/803 X |
| 3,993,049 | 11/1976 | Kater .............................. 128/641 X |
| 4,125,110 | 11/1978 | Hymes .................................. 128/641 |

FOREIGN PATENT DOCUMENTS

| 892944 | 7/1949 | Fed. Rep. of Germany ...... 128/803 |
| 943610 | 10/1956 | Fed. Rep. of Germany ...... 128/803 |
| 1027350 | 2/1953 | France ................................ 128/82.1 |
| 2271846 | 12/1975 | France ................................... 128/803 |
| 2291499 | 6/1976 | France ................................... 128/640 |
| 7206716 | 11/1972 | Netherlands ........................ 128/390 |

*Primary Examiner*—Lee S. Cohen
*Attorney, Agent, or Firm*—Sandler & Greenblum

[57] ABSTRACT

The invention relates to a single-use electroconducting cast forming cutaneous electrode for applying on the human body electric currents for therapeutic or aesthetic treatment, and to a method using same. The cast, such as a mask, is composed of a powder capable of setting with water, such as a plaster as used in dentistry, and of a salt, such as calcium chloride dissolved in the water for setting. Metallic contacts are embedded in the cast for connection to the generator generating current for treatment. A conventional counter-electrode is provided for the return of the current to the generator. The mixture of powder and water for setting which may contain, in addition to the salt, adjuvants such as polyalcohols, protein-containing surface-tension agent and vitamins, is placed in position before the setting begins, and the current for treatment is applied after the beginning of setting. After the setting is complete and the treatment is terminated, the cast is removed and discarded.

15 Claims, 4 Drawing Figures

ELECTROCONDUCTING CAST FORMING A CUTANEOUS ELECTRODE FOR APPLYING ELECTRICAL CURRENTS TO THE HUMAN BODY FOR THERAPEUTIC OR AESTHETIC TREATMENT AND METHOD OF USING SUCH ELECTROCONDUCTING CAST

FIELD OF THE INVENTION

The present invention relates to an electroconducting cast adapted to serve as contact electrode following the contour of the skin of the human body so as to apply thereto, for purposes of therapeutic or aesthetic treatment, electric currents of determined shape and sign delivered by a suitable generator. The invention also relates to a method for using this electroconducting cast.

BACKGROUND OF THE INVENTION

The methods of treatment by passing current through the skin of the human body are known per se and are outside the scope of the present invention. The currents are passed into the skin between one or a plurality of cutaneous electrodes, generally formed by rigid or elastically deformable conducting plates, connected to a first terminal of a generator provided to produce currents of form and direction defined by the method of treatment, and one or more counter-electrodes connected to a second terminal of the generator. The counter-electrodes may be similar to the cutaneous electrodes, or constituted by supple pads impregnated with a physiologically neutral conducting liquid. The action of the currents penetrating in the skin under the cutaneous electrodes is often reinforced by oiling the skin with pharmacologically active compositions, whilst the counter-electrodes used for the return of the currents towards the generator have an essentially neutral behaviour.

It will be specified that the cutaneous electrodes considered in the present case are fundamentally different from electrodes used as contacts intended for recording electric signals of organic origin, such as cardiogram or encephalogram signals, these contacts being very localized and provided to transmit signals of minimum power, whilst the cutaneous electrodes may cover extensive regions of the body and must transmit appreciable powers to the organism, with superficial power densities which are balanced in all the regions involved. Whilst the contacts must aim essentially at minimising the contact potentials, the cutaneous electrodes must aim at the balanced distribution of the currents in the regions involved, under conditions where the contact potentials have a negligible influence.

The current cutaneous electrodes have the drawback that the plates, even if they are elastic, do not strictly follow all the contours of the skin, especially if the regions in question have prominent projections or recesses, or bony ridges or delicate or sensitive parts, where the application of pressures capable of bringing the skin and the electrode into mutual conformation, is unacceptable. Facial treatments are particularly difficult from this point of view. Now, the treatment of the skin is effective only where it is in contact with the cutaneous electrode, so that, with currently used electrodes, there is a risk of irregularities of treatment showing zones with visible boundaries, possibly aggravated by a danger of local burns in zones where there is an excessive concentration of current. Furthermore, the treatment of broad extents of skin, for example from the waist to the ankles, requires a plurality of electrodes which are difficult to place and fix contiguously, and of which the suitably balanced coupling to the generator requires a bulky network of conductors which is difficult to adjust.

French patent application No. 75 15622 describes compositions of electrodes designed to be applied directly on the skin of patients for the purposes of electrical stimulation to act on pain and motricity, which compositions comprise a resinous binding agent with which is mixed a certain quantity of electrically conducting powder, and similar to conducting paints used for industrial electrical applications. The resinous binding agents are chosen such that, under the conditions of use, particularly in solution, they are neither toxic, nor irritant, nor allergenic and adhere to the skin, in three classes comprising acrylovinyl resins, polyether urethanes and polyvinyl acetates, whilst the conducting powders are grains of silver, gold or platinum, or a graphite powder. The compositions are normally positioned in the form of paints with dermatologically acceptable solvents such as acetone, ethanol, isopropanol and the like. As a variant, the acrylovinyl compositions containing silver powder may make adhesive coatings on sheets of paper or metal.

On combining the scattered teachings of the above-mentioned French patent application, it is understood that the cutaneous electrodes form very supple films, whose thickness ranges between a few micrometers to a few tens of millimeters, which are provided to occupy localized zones of the body, such as joints, and typically the wrist, and remain there for several days (three days at minimum) so as to be able to carry out a series of sessions of treatment. The adhesion of the conducting films is determined by a prior degreasing of the skin. Moreover, the cutaneous electrodes thus produced are provided for relatively localized treatments, this resulting from the fact that the skin must be stretched for the application, which can only be effected in restricted zones. Furthermore, the application of continuous films, even having a certain permeability to water vapour, over extensive regions of the body and for several consecutive days, would be capable of provoking skin lesions.

It is therefore appreciated that the cutaneous electrodes described in the above-mentioned French patent application are generally not suitable for replacing the electrodes constituted by rigid or elastic plates mentioned previously in the description of the state of the art for the application of methods of therapeutic or aesthetic treatments by the passage of currents in the skin to which the present invention refers, and which envisage treatments of the skin or subjacent tissues, over extensive regions of the body, including the face.

SUMMARY OF THE INVENTION

It is an object of the invention to provide a cutaneous electrode, adapted to the application of the heretofore mentioned methods, capable of following all the contours of the skin over wide extents of the human body, so as to allow a balanced distribution of the currents for treatment over the whole extent of the skin contacted.

It is also an object of the invention to provide a cutaneous electrode of the preceding type, which, during its application, ensures a general maintenance of the shape of the skin with a certain suppleness allowing small deformation of the skin without loss of contact.

It is a further object of the invention to provide a cutaneous electrode capable of serving a support for adjuvants for treatment.

To these ends, the invention provides a cutaneous electrode for applying on the skin of the human body electric currents for therapeutic or aesthetic treatment thereof, in association with a counter-electrode, said electrode and counter-electrode being coupled respectively to two terminals of a treatment current generator, said electrode being of the type comprising a composition to be applied directly on the skin, solidifying rigidifying after having been placed in position, comprising a mixture of a plastic binding agent and an electrically conducting additive, wherein said electrode is constituted by an electroconducting cast comprising as binding agent a powder binding agent capable of setting with water, and, as conducting additive, a salt dissolved in the water for setting.

The accuracy and fineness of detail of casts made with a powder capable of setting with water of the type such as plaster, currently used for anatomical casts, are known. The incorporation in the water of a soluble calcium salt gives the cast an electrical conductivity due to the ionisation of the salt in the presence of the water for setting in excess over the quantity reacting with the powder during setting.

To establish connections to the current generator, it is preferred to incorporate a metallic contact in the cast, embedding it in the powder-water mixture when the cast is being made.

A plaster as used in dentistry, i.e. a plaster marketed for dental impressions, and a quantity of water for setting which is close, in weight, to half that of the plaster, and containing in solution between 3 and 10% by weight of calcium chloride are preferably used. A paste is thus obtained, by mixing, which allows an easy application, and of which the speed of setting and concomitant rise in temperature are adjustable as a function of the conditions of treatment chosen, by adjusting the quantity of calcium chloride used.

In a preferred solution, the water for setting further contains a protein-containing surface-active product and adjuvants active on the skin. The surface-active product tends to form a foam with the water, thus promoting a spongy structure of the cast, which bears small deformations better. The spongy structure also promotes a migration of the adjuvants and protein-containing components towards the skin of the subject.

The adjuvants comprise polyalcohols containing at the most six carbon atoms, and particularly polypropylene glycol, glycerol and sorbitol which avoid a drying of the skin or have a nourishing effect. Vitamins will also be used as adjuvants, particularly B6, C and PP, which have beneficial effects on the skin.

It is also an object of the invention to provide a method for using an electroconducting cast, constituted by a mixture of powder capable of setting with water and water for setting which contains a calcium salt dissolved therein, according to which method a cutaneous electrode is moulded on the part of the body to be treated before the mixture has set, embedding therein a metallic contact, currents for treatment are applied to this contact after the setting has begun, and at the end of application of the current, the electrode is removed and discarded. In fact, the cast is of reasonable price, with the result that, for each period of treatment, a new cast may be used, whose composition is adjusted to the treatment chosen, which will be adapted exactly to the part of the body to be treated in the very state in which it is at that moment.

The invention will be more readily understood on reading the following description with reference to the accompanying drawings, in which:

DETAILED DESCRIPTION OF THE PREFERRED EMBODIMENTS

Figure 1:
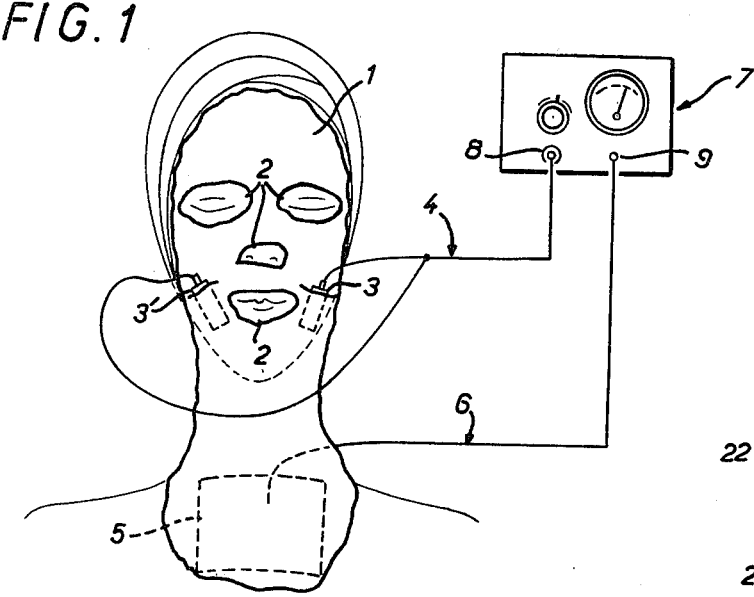
FIG. 1 shows an electroconducting cast in the form of a face mask.

In the embodiment shown in FIG. 1, an electroconducting cast 1, made of plaster of which the water used for setting contains, in solution, calcium chloride and adjuvants, as will be described in greater detail in Examples 1 and 2 hereafter, is applied on the face of a subject, descending over the front part of the neck. The cast comprises gaps 2 for the eyes, nostrils and lips. Two metallic conductors 3 and 3' are incorporated in the cast 1, at cheek level, and are connected to a common conductor 4. A counter-electrode 5, constituted by a pad of absorbent tissue impregnated with a conducting liquid, such as a glycerinated physiological serum, and lined with a supple metal foil towards the outside, is applied on the subject's back, between the shoulder blades. The counter-electrode 5 is provided with a connecting conductor 6. A generator 7 generating currents for therapeutic or aesthetic treatment, of known type and provided for this use, comprises a terminal 8 for the output of currents for treatment and a terminal 9 for the return of current. Output and return of the currents for treatment are not to be understood here in the conventional sense of circulation of the current from a positive terminal to a negative terminal, but in the sense of the currents which produce a therapeutic or aesthetic action on penetrating the skin, from the output terminal 8 of the generator 7, passing through the electroconducting cast 1, whilst the current leaving the body via the counter-electrode 5 for returning to the generator 7 via terminal 9 produces virtually no physiological action.

The cast is made by mixing dental plaster with water for setting containing, in solution, calcium chloride and adjuvants, as will be explained in greater detail in the Examples hereinafter; when the mixture begins to harden or rigidify it is applied in a layer of a few millimeters thickness on the skin of the face, previously oiled with a known composition or cream, leaving gaps 2 for the eyes, nostrils and lips, as is conventional in the application of face masks. Oiling with cream is intended to soften the contact of the cast with the skin, and also to contribute to the treatment by supplying active components.

The conductors 3, 3' are placed in position and covered with an extra thickness of mixture, sufficient pressure being applied to ensure the interpenetration of the successive beds of mixture. The conductors 3 and 3' are then coupled to terminal 8 via conductor 4, and the counter-electrode 5 connected to terminal 9 is placed in position, adhesive strips ensuring a good contact of the counter-electrode 5 on the skin. When the mixture begins to set, this being marked by a heating of the cast, the generator 7 is switched on, and adjusted to obtain the desired conditions of treatment. As will be specified hereinafter, the composition of the cast is adjusted to regulate the speed of setting, as a function of the duration of the treatment, so that the treatment terminates when setting is completed. At the end of the treatment, the cast is detached from the face by contraction of the muscles, as resulting from a smile. It may be observed that the cast reproduces the details of contour of the skin with considerable fineness; this showing that the contact of the electroconducting cast on the skin during the treatment extended over the whole surface of the mask.

Figure 2A:
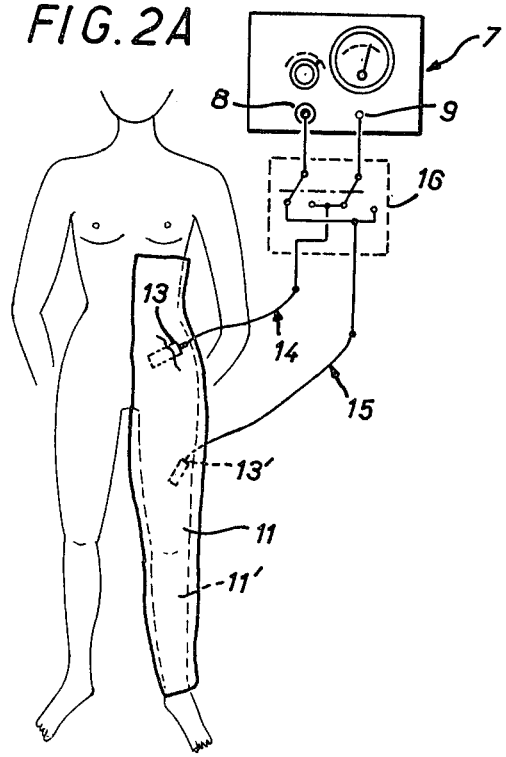
FIG. 2A shows an electroconducting cast applied between waist and ankle of a subject seen in front view.
Figure 2B:
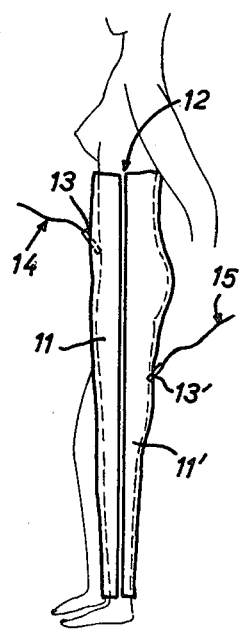
FIG. 2B shows the cast of FIG. 2A, but seen in side view.

The cutaneous electrodes intended for the treatment by electric currents of extensive parts of the body may be constituted as shown in FIGS. 2A and 2B, where the treatment concerns the left-hand part of the body between the waist and the ankle. The electroconducting cast, of which the composition will be described in greater detail with reference to Example 3, is constituted in two parts, a front part 11 and rear part 11', separated by a break 12, substantially in a plane transverse with respect to the subject. In FIG. 2B, where the subject is seen in profile, the break 12 is seen extending from the waist to the ankle following a line on the outer faces of the hip and the leg, but it is understood that this break 12 extends (not shown in the Figures) from the ankle to the pubis following the inner faces of the calf and thigh. In the front part 11 of the electroconducting cast is embedded a conductor 13, and in the rear part 11' is embedded a conductor 13', the conductors 13 and 13' being extended respectively by connecting cables 14 and 15. The connecting cables 14 and 15 are connected to the terminals 8 and 9 of the generator 7 through an inverter 16, so that the parts 11 and 11' of the cast may be coupled alternately, or respectively, to the current output and return terminals 8 and 9 or to terminals 9 and 8. Thus, the parts 11 and 11' of the cast may act alternately as cutaneous electrode and counter-electrode, by manuevering the inverter 16, the subjacent front and rear regions of the body being treated alternately. The mixing of the cast mixture, the preparation of the electroconducting cast and the treatment are the same as described with reference to FIG. 1.

At the end of the session of treatment, the casts are removed. The removal of the cast frequently involves destruction thereof. In any case it is without interest, particularly due to the reasonable price of the constituents of the cast, to reuse it for a subsequent session of treatment, apart from the fact that it is highly unlikely that a previously made cast will suitably follow the contours of the skin on a subsequent occasion. The casts are therefore considered as being for "once only" use and are systematically discarded after a session of treatment.

Figure 3:
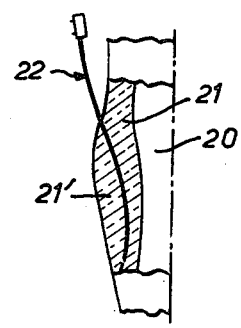
FIG. 3 shows a detailed view of the cast with an embedded contact.

As is clearly shown in FIG. 3, the embedding of the coupling conductors 22 is effected by applying on the skin 20 a first layer 21 of setting mixture. On this first layer 21 is applied the conductor 22, composed of metal braid, which imprints itself in the fresh layer 21, and the end of this conductor 22 is covered by a second layer 21' of mixture, sufficient pressure being applied to ensure that the layers 21 and 21' stick to each other, imprisoning the braid 22 therebetween.

Examples of composition of the electroconducting cast will now be described.

EXAMPLE 1

Mask for Lack-Luster Skin 400 grams of dental plaster with a setting time of 5 to 10 min. are mixed with 200 g of water for setting at 25° C., in which are dissolved:

| | |
|---|---|
| Calcium chloride | 8 g |
| Glycerine | 5 g |
| Lipoproteol* | 1 g |
| Vitamins B6 and C | 0.2 g |

*Lipoproteol is a Trademark designating a surface-active agent containing amino acids (proteins).

The foam which is formed at mixing by the presence of the surface-active agent increases the porosity and consequently the suppleness of the cast during setting; the amino acids, which are ionisable, will migrate under the influence of the current for treatment towards the skin which will be nourished thereby.

This cast composition sets fairly rapidly, this being accompanied by a marked heating.

Before the application of the cast, the skin of the face is oiled with a known nourishing and moisturizing cream having the following composition:

| | | |
|---|---|---|
| Beeswax | | 24 g |
| Cetyl alcohol | | 56 g |
| Amphisol (Trademark) | | 8 g |
| Thick vaseline | | 80 g |
| Lanolin | | 40 g |
| Oleic alcohol | | 40 g |
| Isopropyl myristate | | 80 g |
| Nipastat (Trademark) | | 2.4 g |
| Butylhydroxy toluene | | 0.4 g |
| Water | | 410 g |
| Borax | | 8 g |
| Linden extract | | 10 g |
| Phenonip (Trademark) | | 2.4 g |
| | for about | 760 g. |

EXAMPLE 2

Mask for Sensitive Skins 400 g of dental plaster with a setting time of 10–15 min. are mixed with 200 g of water for setting at 18° C., in which are previously dissolved:

| | |
|---|---|
| Calcium chloride | 16 g |
| Propylene-Glycol | 10 g |
| Lipoproteol (Trademark) | 1 g |
| Vitamins PP and C | 0.2 g |

The mixture has a substantially increased setting time and a rise in temperature during setting which is substantially less than the mixture of Example 1, due in particular to the relatively high content of calcium chloride. The lipoproteol has the same effect as in Example 1, and the propylene-glycol acts like the glycerol of the preceding Example. The vitamins are chosen to be adapted to the type of skin in question.

Before the application of the mask, the skin of the face will be oiled with a suitable cream, of known composition as follows:

| | |
|---|---|
| Butyl stearate | 80 g |
| Thick vaseline oil | 49.6 g |
| Dodecanol | 80 g |

-continued

| Cetyl alcohol | 32 g |
| --- | --- |
| Amphisol (Trademark) | 24 g |
| Sweet-almond oil | 32 g |
| Butylhydroxytoluene | 0.8 g |
| Nipastat (Trademark) | 2.4 g |
| Water | 350 g |
| Sorbitol | 48 g |
| Glycerine | 80 g |
| Methylrutin | 0.8 g |
| Floral hamamelis compound | 24 g |
| Azulene | 0.8 g |
| Phenonip (Trademark) | 2 g |
| Perfume | 1.6 g |
| for about | 800 g. |

EXAMPLE 3

Electroconducting Cast for the Body 4000 g of dental plaster with a setting time of 10-15 min. are mixed with 2000 g of water at 30° C. containing, in solution:

| Calcium chloride | 100 g |
| --- | --- |
| Solbitol | 50 g |
| Lipoproteol | 5 g |
| Galactan sulphate | 5 g |

The sorbitol, which is an itol derived from a hexose, is therefore a polyalcohol with six atoms of carbon, has an anti-drying power similar to that of the glycol and glycerol of the preceding Examples, added to a nourishing power due to its formula close to that of a sugar. The lipoproteol is foaming and contributes its proteins. The galactan sulphate plays a slenderizing role.

The cast made with this mixture rests supple enough to support, for at least 15 min. the excitomotor movements (muscular reactions to the electric currents for treatment) without breaking.

Before application of the cast, the body will be oiled in the regions involved with a moisturing treating product of known composition, such as:

| Water | 1470 g |
| --- | --- |
| glycerine | 20.8 g |
| Bronidox (Trademark) | 0.24 g |
| Phenonip (Trademark) | 1 g |
| Galactan sulphate | 48 g |
| Carbopol (Trademark) | 40 g |
| Dye | 0.8 g |
| Perfume | 1.34 g |
| Triethanolamine | 43.8 g |
| for about | 1600 g. |

Complementary tests have verified that, depending on the content of calcium chloride in the water, varying between 3 and 10% by mass with respect to the water, the setting speed varied, reducing when the calcium chloride content was increased; concurrently, the heating of the cast during setting varies with the setting speed. The duration of treatment must be of the same order as the duration of complete setting so that the conductivity of the cast, its relative suppleness, and the freedom of migration of the adjuvants dissolved in the water remain sufficient to ensure the efficacy of the treatment, so that it is clear that the desired duration of the treatment determines the speed of setting and therefore the concentration of calcium chloride in the water, which will be specified by routine tests.

What is claimed is:

1. A cutaneous electrode comprising a rigid electroconductive cast comprising a powder capable of setting with water, water present in an amount greater than that necessary to set with said powder, said water containing a salt dissolved therein in a sufficient quantity to impart electrical conductivity to said rigid cast, and a metallic contact embedded within said cast and adapted to be connected to a current generator, said rigid cast conforming closely to the shape of a predetermined skin contour, said cast being formed by molding to said skin contour prior to complete setting of said cast, and said metallic contact being embedded within said cast prior to complete setting of said cast.

2. The electrode of claim 1 wherein said powder comprises dental plaster, the amount of water comprising approximately half the weight of the plaster, and said salt is calcium chloride and comprises between 3 and 10% by weight of said water.

3. The electrode of claim 2, wherein the water for setting further contains a protein-containing surface-active agent and adjuvants active on the skin.

4. The electrode of claim 3, wherein the adjuvants comprise a polyalcohol containing at the most six atoms of carbon.

5. The electrode of claim 4, wherein said polyalcohol is chosen from the group consisting of polypropyleneglycol, glycerol and sorbitol.

6. The electrode of claim 3, wherein the adjuvants comprise at least one vitamin chosen from the group consisting of vitamins B6, C and PP.

7. The electrode of claim 1, wherein said cast comprises two parts divided by a separating break, each part being adapted to be respectively coupled to one of two terminals of a generator.

8. A system adapted to supply electric current for therapeutic or aesthetic treatment to a human skin contour, said system comprising:
(a) an electrode comprising a composition adapted to be applied directly to said skin, said composition adapted to rigidify after said placement and comprising a powder binding agent settable with water, said powder binding agent comprising dental plaster, water present in an amount larger than that sufficient to rigidify and set with said powder and comprising approximately half of the weight of said plaster, and a dissolved salt comprising calcium chloride and present in a sufficient quantity to impart electrical conductivity to said electrode, said calcium chloride comprising between 3 and 10% by weight of said water, whereby when said composition rigidifies a rigid electroconductive cast results which closely follows said skin contour and is therefore capable of distributing current equally over said contour;
(b) a treatment current generator; and
(c) a counterelectrode, said electrode and said counterelectrode coupled to two terminals of said treatment current generator.

9. A system in accordance with claim 8 wherein said cast comprises two parts divided by a separating break, each part being respectively coupled to one of the two terminals of said generator whereby one of said two parts acts as said counterelectrode.

10. A system in accordance with claim 9 further comprising an inverter means for coupling said two cast parts in a first position in which said parts are attached to first and second terminals of said generator, respectively, and in a second position in which said parts are attached to second and first terminals of said generator, respectively.

11. A system of claim 8 wherein the water for setting further contains a protein-containing surface-active agent and adjuvants active on the skin.

12. A system in accordance with claim 11 wherein the adjuvants comprise a polyalcohol containing, at the most, six atoms of carbon.

13. A system in accordance with claim 12 wherein said polyalcohol is chosen from the group consisting of polypropyleneglycol, glycerol, and sorbitol.

14. A system in accordance with claim 11 wherein the adjuvants comprise at least one vitamin chosen from the group consisting of Vitamins $B_6$, C, and PP.

15. A method for using a cutaneous electrode for applying electric current to human skin contour for therapeutic or aesthetic treatment, said method using an electroconductive cast comprising a powder capable of setting with water, water present in an amount greater than that necessary to set with said powder, said water containing a salt dissolved therein in sufficient quantity for imparting electrical conductivity to said cast and a metallic contact embedded in said cast and adapted to be connected to a current generator, said method comprising:

(a) molding said cast to a part of said skin contour before said cast sets;
(b) embedding said metallic contact in said cast prior to complete setting of said cast;
(c) applying current to said contact; and
(d) removing and discarding said cast from said skin after applying said current.

* * * * *

UNITED STATES PATENT AND TRADEMARK OFFICE
CERTIFICATE OF CORRECTION

PATENT NO. : 4,317,457
DATED : March 2, 1982
INVENTOR(S) : Jacqueline GUILLOT

It is certified that error appears in the above—identified patent and that said Letters Patent is hereby corrected as shown below:

Abstract, line 2, after "forming", insert --a--.
Abstract, line 4, after "using", insert --the--.
Abstract, line 7, after "chloride", insert --,--.
Abstract, line 14, change "agent" to --agents--.
Column 1, line 13, change "the raputic" to --therapeutic--.

Signed and Sealed this

First Day of June 1982

[SEAL]

Attest:

GERALD J. MOSSINGHOFF

Attesting Officer    Commissioner of Patents and Trademarks